United States Patent [19]

Nelson

[11] 4,237,874
[45] Dec. 9, 1980

[54] ANKLE BRACE

[76] Inventor: Ronald E. Nelson, 100 S. Main St., Cambridge, Minn. 55008

[21] Appl. No.: 79,785

[22] Filed: Sep. 28, 1979

[51] Int. Cl.³ .............................................. A61F 3/00
[52] U.S. Cl. .................................... 128/80 H; 128/166
[58] Field of Search ............................. 128/80 H, 166

[56] References Cited

U.S. PATENT DOCUMENTS

| | | | |
|---|---|---|---|
| 1,084,197 | 1/1914 | Collis | 128/166 |
| 2,994,322 | 8/1961 | Cullen et al. | 128/80 H |
| 3,073,305 | 1/1963 | Biggs, Jr. et al. | 128/166 |

Primary Examiner—John D. Yasko
Attorney, Agent, or Firm—Burd, Bartz & Gutenkauf

[57] ABSTRACT

An ankle brace for use by athletes or others requiring ankle support. The brace includes a base that is conformable to the foot and ankle region of the wearer. Flexible upright side support members are secured to either side of the base in such a fashion to form a plurality of elongate upright parallel pockets. Resilient stiffening ribs are located in the pockets positioned to straddle the lateral malleolus and the medial malleolus. Flexible intermediate transverse members are secured on either side to the upright side support members in the vicinity of the ankle bone to provide additional support. The lower interior of the base is concave to conform to the arch.

16 Claims, 11 Drawing Figures

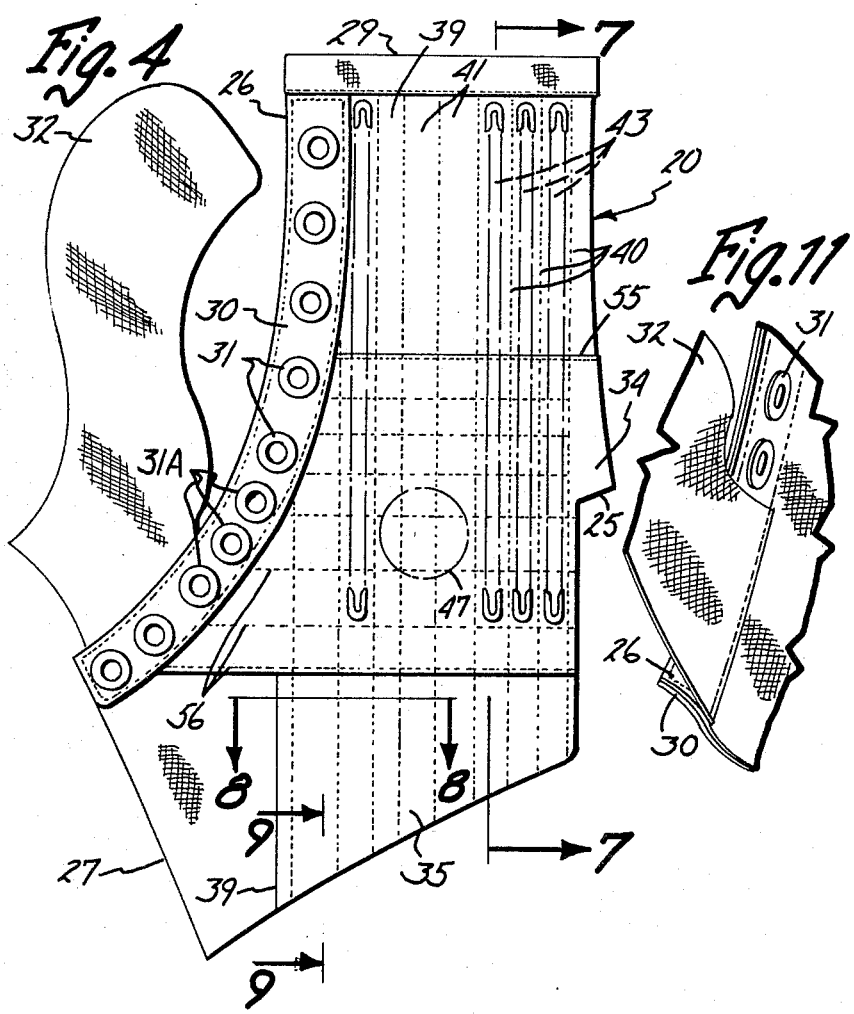
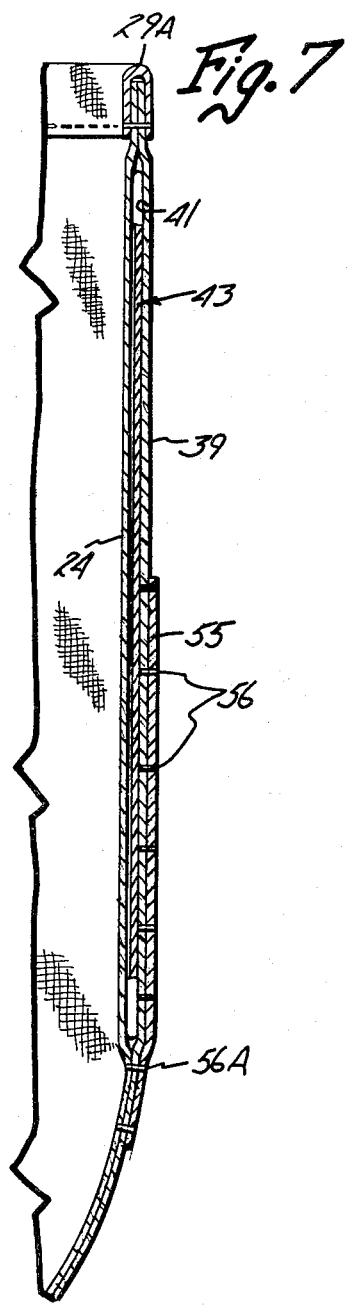
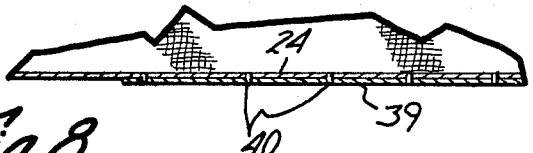
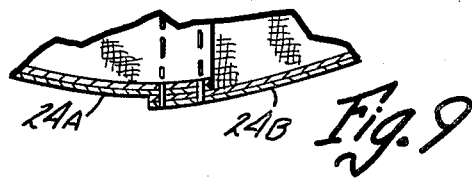
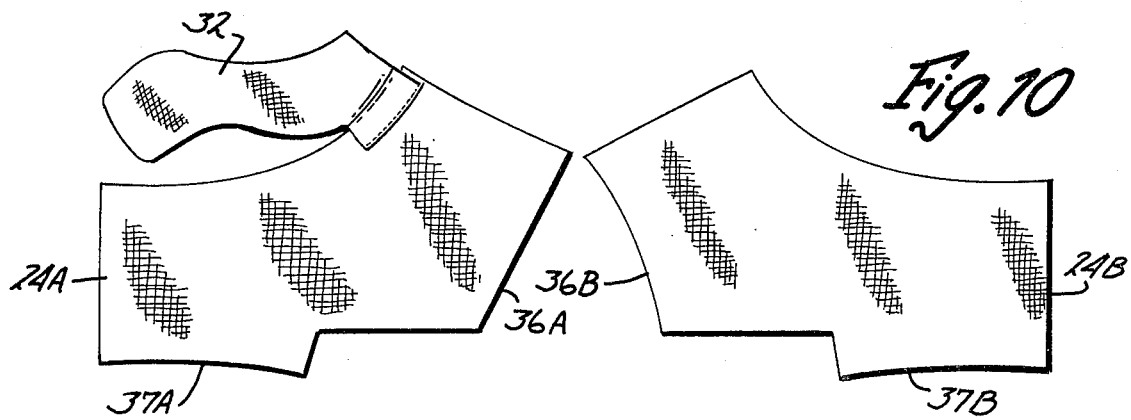

ANKLE BRACE

BACKGROUND OF THE INVENTION

In athletics it is common practice for the athlete to have his ankle and foot wrapped or taped in order to prevent injury and in order to prevent aggravation of a pre-existing injury. It is desirable to inhibit rotation of the ankle about a longitudinal axis parallel to the foot and, to some extent, to inhibit normal flexure of the foot and ankle.

The use of adhesive tape for this purpose has certain disadvantages. It is time consuming as well as expensive as the tape is not reusable. The tape can have a propensity to loosen and slip responsive to perspiration. Elastic bandages are also used but these do not give as much support as adhesive tape.

The invention relates to an ankle brace for use by athletes or others requiring ankle support. The brace includes a base that can be wrapped around the foot and laced up the front. The lower interior or lower medial portion of the base as it wraps around the instep is concave to more closely conform to the foot. Flexible upright side support members are secured to either side of the base substantially the entire heighth of the base in such a fashion to form a plurality of elongate vertical pockets. Resilient stiffening ribs are located in the pockets to hold the base up with respect to the ankle and lower leg and provide a measure of support. The ribs or stays are spaced to straddle the lateral malleous or outer angle bone on the outer portion of the base, and to straddle the medial malleolus or inner ankle bone on the inner portion of the base. A flexible intermediate transverse member is secured on each side to the upright side support members in the vicinity of the ankle bone to provide additional support in the vicinity of the ankle joint.

IN THE DRAWINGS

FIG. 4 is an enlarged side elevational view of the ankle brace of FIG. 1 showing the medial or interior side thereof;

FIG. 7 is an enlarged sectional view of a portion of the ankle brace shown in FIG. 4 taken along the line 7—7 thereof;

FIG. 8 is an enlarged sectional view of a portion of the ankle brace of FIG. 4 taken along the line 8—8 thereof;

FIG. 9 is an enlarged sectional view of a portion of the ankle brace of FIG. 4 taken along the line 9—9 thereof;

FIG. 10 is a diagrammatic view of two pieces of material that can be joined together in one method of forming the base of the ankle brace of the invention; and FIG. 11 is an enlarged view of a portion of the ankle brace showing the attachment of the tongue to the base.

DESCRIPTION OF PREFERRED EMBODIMENT

Figure 1:
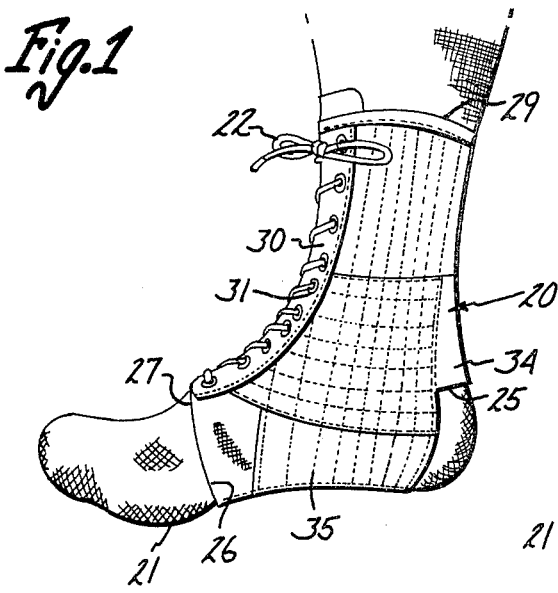
FIG. 1 is a side elevational view of an ankle brace according to the invention being worn on a foot of a person.
Figure 2:
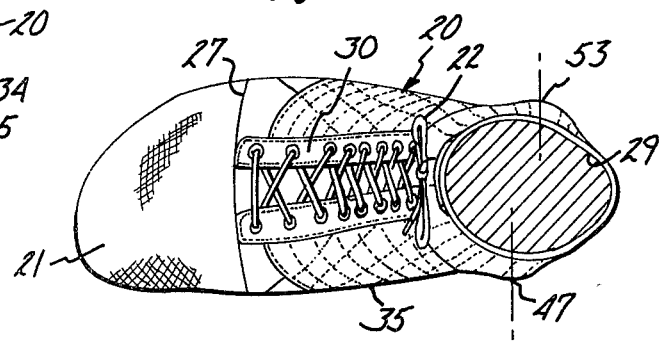
FIG. 2 is a top plan view of the ankle brace and foot of FIG. 1.

Referring to the drawings, there is shown in FIGS. 1 and 2 an ankle brace 20 being worn on the lower right ankle and foot 21 of a wearer held securely thereon by lacing 22 in supportive relationship to the ankle joint. The ankle joint is the joint between the leg and foot in which the tibia and fibula above articulate with the talus below. The ankle is the region of the ankle joint. Ankle brace 20 supports the ankle of the wearer with respect to the foot and lower leg so as to inhibit rotation or twisting about a longitudinal axis parallel to the lengthwise dimension of the foot and, to some extent, inhibit the normal flexure between the foot and lower leg.

Ankle brace 20 includes a base 24 of durable, flexible sheet material such as vinyl bonded to filament nylon mesh. Base 24 is configured to encompass the ankle joint and the ankle or adjacent lower leg portion, and the rear portion of the foot encompassing the arch and the instep. The heel of the foot is accommodated in a heel opening 25. Closable forward edges 26 of base 24 come together along the front superior foot surface and the front lower leg portion forming a front opening 27, through which extends the toes and front ball portion of the foot. An upper edge 29 encircles the leg.

Reinforcing strips 30 are sewn to the front edges 26 and carry eyelets 31 defining openings for receipt of lacing 22. Lacing 22 is laced in and out of the eyelets 31 in the usual fashion and can be tied at the upper portion in a bow knot. Eyelets 31 are spaced apart along the forward edges 26 and are more closely spaced as the eyelets 31A, in the vicinity of the ankle joint and the front superior foot surface. The closer spacing of the eyelets 31A in that vicinity provides a greater measure of support upon normal flexure between the foot and lower leg portion. A tongue 32, as shown in FIG. 11, is sewn to a portion of a forward edge 26 positioned to cover the front superior foot surface and forward lower leg portion in the usual fashion when the lacing 22 is secured. The rear portion of base 24 above heel opening 25 is outwardly curved as at 34 to closely accommodate the anterior curve of the rear foot portion superior to the calcaneus for closer conformance of the ankle brace 20 to the lower leg and foot.

The lateral or exterior lower side of base 24 is formed flat so as to be conformable to and bend around the lateral foot portion into the instep. The medial or interior lower portion of the base 24 is formed concave as at 35 in FIGS. 1 and 2 so as to closely conform to the arch of the wearer. A method of so forming base 24 can be seen with reference FIG. 10 which shows two separate pieces for forming the base 24 comprised as a piece 24A to form the lateral side and a second piece 24B to form the medial side. The intended lower edge 36A of lateral piece 24A is straight. The intended lower edge 36B of medial piece 24B is curved inwardly or concave. The two edges 36A, 36B are joined as by sewing (See FIG. 9) and as a result of the curvature of the medial lower edge 36B, the concave portions 35 if formed. Base 24 is completed by joining the intended rear edges 37A, 37B as by sewing them together.

Figures 5, 6:
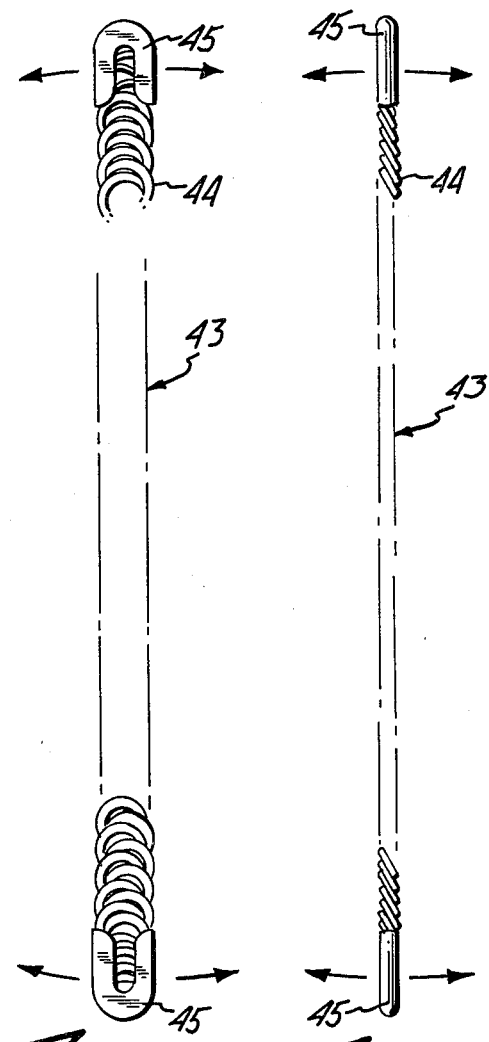
FIG. 5 is an enlarged front plan view of one form of a resilient stiffening rib or stay usable in the ankle brace of the invention.
FIG. 6 is a side elevational view of the flexible stiffening rib or stay of FIG. 5.

As shown in FIGS. 4 and 7, a medial flexible upright support member 39 is fixed to the medial side of base 24 extending from the bottom thereof to the upper edge 29. Support member 39 is sewn to base 24 by a plurality of upright seams 40 to form a plurality of parallel, upright pockets 41 between base 24 and flexible support member 39. An inverted U-shaped flap 29A is sewn along the upper edge 29 of base 24 to join base 24 and upright support member 39 at the upper extremity. A plurality of medial elongate resilient stiffening ribs or stays 43 are located in select pockets 41. Stays 43 serve to keep base 24 and upright support member 39 erect to avoid downward creeping, and also serve to impart an additional measure of support to the ankle. As shown in FIGS. 5 and 6, each stay 43 can be comprised of two helical spring elements interleaved and flattened having an elongated coiled body portion 44 with end caps 45. As so constituted, stays 43 are resiliently flexible in all directions, as noted by the arrows in FIGS. 5 and 6.

Medial stays 43 are spaced apart to straddle the area which covers the medial malleolus or that portion of the ankle bone that extends from the tibula as indicated at the area 47 in FIG. 4. As shown, three stays 43 are located rearwardly of the area 47 and one stay is located forwardly of it for purposes of comfort to the wearer and to maximize the effectiveness of the stays.

Figure 3:
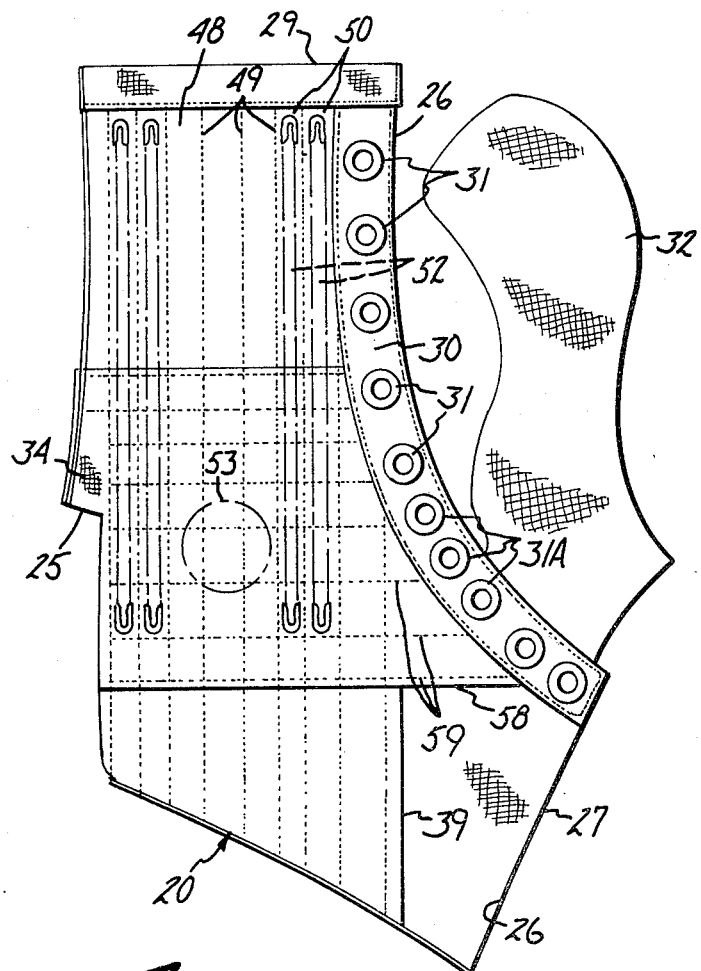
FIG. 3 is an enlarged side elevational view of the ankle brace of FIG. 1 showing the lateral or exterior side of the ankle brace.

As shown in FIG. 3, a lateral flexible upright support member is fixed to the lateral side of base 24 extending from the bottom thereof to the upper edge 29. Support member 48 is sewn to base 24 by a plurality of parallel upright seams 49 to form a plurality of parallel, upright pockets 50 between base 24 and flexible support member 48. A plurality of lateral elongate resilient stiffening ribs or stays 52 are located in select pockets 50. Lateral stays 52 can be constructed like the medial stays 45. Lateral stays 52 are spaced apart to straddle the area covering the lateral malleolus or that portion of the ankle bone that extends from the fibula as indicated at the area 53 in FIG. 3. As shown in FIG. 2, the medial malleolus, indicated at 47, is located slightly ahead of the lateral malleolus, indicated at 53. For this reason, as shown in FIG. 3, two lateral stays 52 are located rearwardly of the area 53, and two stays 52 are located ahead of it whereby the area 53 provided to accommodate the lateral malleolus is located slightly behind the area 47 provided to accommodate the medial malleolus. This is for purposes of comfort to the wearer and to maximize the effectiveness of the lateral stays 52.

As shown in FIGS. 4 and 7, a medial transverse flexible support member 55 is fixed to the medial upright support member 39 in the vicinity of the area 47 for accommodation of the medial malleolus. Transverse support member 55 extends from proximate the front edge 26 of base 24 to the rear thereof and has upper and lower edges intermediate the upper and lower edges of upright support member 39. Transverse support member 55 is fastened to the upright support member 39 with a plurality of parallel transverse seams 56 in perpendicular relationship to the upright seams 40. Upright seams 40 are sewn through the transverse support and the upright support and attached to the base, while the transverse seams 56 are sewn only between the upright support member 39 and the transverse support 55 so as not to interfere with the pockets 41. A lower transverse seam 56A as shown in FIG. 7 attaches to the base 24 to form a bottom for the pockets 41. The criss-cross or checkered pattern provided by the upright seams 40 and the transverse seams 56 provides additional support in the vicinity of the medial malleolus.

As shown in FIG. 3, on the lateral side of base 24 is a lateral flexible transverse support member 58 affixed to the lateral upright support member 48 by transverse seams 59. Lateral transverse support member 58 is fixed to the lateral upright support member 48 and base 24 in the same fashion that the medial transverse support member 55 is fixed to the medial upright support member 39 and base 24 whereby additional support is provided in the vicinity of the lateral malleolus.

In the use of the ankle brace, the athlete normally wears one on each foot, the left foot version being just opposite that shown in the drawings. Lacing 22 is loosened to an extent whereby the athlete can slip his foot through the opening defined by top edge 29 and insert his toes through the front opening 27 with the heel resting in the heel opening 25. The arch is supported in the concave portion 35 of base 24. When lacing 22 is tightened, support is provided by the base 24 as well as the lateral and medial upright support members 48, 39 and the corresponding resilient stays 52, 43. In the vicinity of the malleolus, additional support is provided by the lateral and medial transverse support members 58, 55. The foot is inhibited from twisting or rotating with respect to the lower leg about an axis parallel to the longitudinal dimension of the foot. In addition, normal flexure between the foot and the lower leg portion is somewhat inhibited. The curvature 34 at the rear of base 24 and the concave curvature 35 at the instep permit close comformance of the brace to the foot and ankle of the wearer. The closely grouped eyelets 31A on the superior forward portion of the foot lend additional support there against flexure between the foot and lower leg.

The embodiments of the invention in which an exclusive property or privilege is claimed are defined as follows:

1. An ankle brace to be worn on a foot and ankle encompassing the lateral and medial sides of a foot and an ankle having respectively a lateral malleolus and a medial malleolus, in supportive relationship to the ankle joint, comprising:

a base of flexible sheet material shaped to encompass an ankle and at least the middle portion of a foot;

a medial flexible upright support member fixed to the medial side of the base by parallel upright seams extending from the lower portion of the base to an upper edge of the base surrounding the ankle;

a flexible medial transverse support member fixed to the medial upright support member in the vicinity covering the medial malleolus of the ankle, by a plurality of parallel transverse seams generally perpendicular to the upright seams on the medial upright support member;

a lateral flexible upright support member fixed to the lateral side of the base by upright parallel seams extending from the lower portion of the base to the upper edge of the base surrounding the ankle; and a flexible lateral transverse support member fixed to the lateral upright support member in the vicinity covering the lateral malleolus of the ankle, by a plurality of parallel transverse seams generally perpendicular to the upright seams on the lateral upright support member.

2. the ankle brace of claim 1 wherein: the seams fixing the upright lateral and medial support members to the base form a plurality of upright lateral and medial pockets; a plurality of resilient medial stays located in selected medial pockets spaced to straddle an area of the base encompassing the medial malleolus; and a plurality of resilient lateral stays located in selected lateral pockets spaced to straddle an area of the base encompassing the lateral malleolus.

3. The ankle brace of claim 2 wherein: the area straddled by the medial stays encompassing the medial malleolus is located longitudinally forward of the area straddled by the lateral stays encompassing the lateral malleolus.

4. The ankle brace of claims 1 or 2 wherein: the lower medial portion of the base is concave in order to conform to the arch of a foot.

5. The ankle brace of claims 1 or 2 wherein: said base has forward edges defining an opening closable about the front of the ankle and foot, a plurality of spaced apart eyelets with eyelet openings on the forward edges, a lacing laced through the eyelet openings to secure the forward edges in a closed position, said eyelet openings being more closely spaced on the forward edges toward the center thereof on the forward superior surface of the foot proximate the longitudinal vicinity of the ankle joint to provide additional support at that area.

6. An ankle brace to be worn on a foot and ankle in supportive relationship to the ankle joint comprising:
flexible base means comformable to the ankle and foot of a wearer and having a lateral side on the lateral side of the foot and a medial side on the medial side of the foot;
a flexible medial upright support member fixed to the medial side of the base means extending from the bottom of the medial side of the base means to the top of the medial side of the base means and fixed by means forming a plurality of generally upright medial pockets between the medial upright support member and the base means;
a plurality of resilient stays in selected medial pockets spaced to straddle an area of the base means encompassing the medial malleolus;
a flexible lateral upright support member fixed to the lateral side of the base means extending from the bottom of the lateral side of the base means to the top of the lateral side of the base means and fixed by means for forming a plurality of generally upright lateral pockets between the lateral upright support member and the base means; and
a plurality of resilient lateral stays in selected lateral pockets spaced to straddle an area of the base means encompassing the lateral malleolus.

7. The ankle brace of claim 6 wherein: the means for fixing the lateral and medial upright support members to the base means comprises parallel upright seams forming said lateral and medial pockets, and including a flexible medial transverse support member fixed to the flexible medial upright support member by a plurality of parallel transverse seams in the vicinity of the area of the base means encompassing the medial malleolus, and a flexible lateral transverse support member fixed to the flexible lateral upright support member by a plurality of parallel transverse seams in the vicinity of the area of the base means encompassing the lateral malleolus.

8. The ankle brace of claim 7 wherein: said resilient stays are constituted as helical spring elements interleaved and flattened.

9. The ankle brace of claim 6 wherein: the stays are elongated resilient spring means located in said medial upright pockets and upright lateral pockets.

10. The ankle brace of claim 6 wherein: said base means has edge means defining an opening closable about a front portion of the ankle and foot, and means for holding the edge means in a closed position to locate the base means on the ankle and foot of a wearer and provided additional support about the ankle joint.

11. An ankle brace to be worn on a foot and ankle in supportive relationship to the ankle joint, said ankle having a medial and lateral malleolus, comprising:
flexible base means comformable to the ankle and foot of a wearer and having a lateral side on the lateral side of the foot and a medial side on the medial side of the foot;
a flexible medial upright support member fixed to the medial side of the base means extending from the bottom of the medial side of the base means to the top of the medial side of the base means and fixed by means forming generally upright medial pocket means between the medial upright support member and the base means;
first resilient means located in said medial pocket means spaced to straddle an area of the base means encompassing the medial malleolus;
a flexible lateral upright support member fixed to the lateral side of the base means extending from the bottom of the lateral side of the base means to the top of the lateral side of the base means and fixed by means for forming generally upright lateral pocket means between the lateral upright support member and the base means;
second resilient means in selected generally upright lateral pockets spaced to straddle an area of the base means encompassing the lateral malleolus; and
flexible transverse support means fixed to the medial and lateral upright support members in the vicinity covering the medial and lateral malleolus of the ankle.

12. The ankle brace of claim 11 wherein: the means for fixing the lateral and medial upright support members to the base means comprises parallel upright seams forming said lateral and medial pocket means.

13. The ankle brace of claim 12 wherein: said first and second resilient means are elongated resilient spring means.

14. The ankle brace of claim 11 wherein: said first resilient means include first elongated resilient spring means adapted to be located on one side of the medial malleolus and second elongated resilient spring means adapted to be located on the opposite side of the medial malleolus.

15. The ankle brace of claim 11 wherein: the resilient means comprise first resilient spring means located on one side of the lateral malleolus and second resilient springs located on the opposite side of the lateral malleolus.

16. The ankle brace of claim 11 wherein: said base means has edge means defining an opening closable about a front portion of the ankle and foot, and means for holding the edge means in a closed position to locate the base means on the ankle and foot of a wearer and to provide additional support about the ankle joint.

* * * * *

UNITED STATES PATENT AND TRADEMARK OFFICE
CERTIFICATE OF CORRECTION

PATENT NO. : 4,237,874
DATED : December 9, 1980
INVENTOR(S) : Ronald E. Nelson

It is certified that error appears in the above-identified patent and that said Letters Patent are hereby corrected as shown below:

Column 1, line 31, "malleous" should be --malleolus--

Column 1, line 32, "angle" should be --ankle--

Column 2, line 61, "portions" should be --portion--

Column 6, line 9, "provided" should be --provide--

Signed and Sealed this

Sixteenth Day of February 1982

[SEAL]

Attest:

GERALD J. MOSSINGHOFF

Attesting Officer

Commissioner of Patents and Trademarks